United States Patent [19]

Goliaszewski et al.

[11] Patent Number: 4,666,632
[45] Date of Patent: May 19, 1987

[54] PROCESS FOR THE PREPARATION OF ANTHRAQUINONE

[75] Inventors: Alan E. Goliaszewski, Palmyra; Richard F. Salinaro, Madison, both of N.J.

[73] Assignee: The Halcon SD Group, Inc., Montvale, N.J.

[21] Appl. No.: 883,229

[22] Filed: Jul. 8, 1986

[51] Int. Cl.$^4$ .................. C07C 50/18; B01J 31/36; B01J 31/38
[52] U.S. Cl. ................... 260/369; 502/162; 502/168; 502/208; 502/508; 502/102
[58] Field of Search ................ 260/364; 502/162, 168, 502/208, 508, 102

[56] References Cited

U.S. PATENT DOCUMENTS

| 2,401,225 | 5/1946 | Caesar et al. | 260/369 |
| 4,036,860 | 7/1977 | Engelbach et al. | 260/369 |
| 4,045,456 | 8/1977 | Merger et al. | 260/369 |
| 4,379,092 | 4/1983 | Devic | 260/369 |
| 4,459,234 | 7/1984 | Kawamata et al. | 260/369 |

FOREIGN PATENT DOCUMENTS

| 5731637 | 7/1980 | Japan | 260/369 |
| 5770833 | 10/1980 | Japan | 260/369 |
| 5770832 | 10/1980 | Japan | 260/369 |

OTHER PUBLICATIONS

Kirk-Othmer, Encyclopedia of Chemical Technology, 1978, 3rd ed., vol. 2, pp. 702-707.
Hino, J. Chem. Soc., Chem. Commun., 1985, p. 112.

Primary Examiner—Glennon H. Hollrah
Assistant Examiner—Raymond Covington
Attorney, Agent, or Firm—Harold N. Wells

[57] ABSTRACT

Anthraquinone is produced by reacting phthalic anhydride with benzene in the liquid phase over a super acid catalyst which may be an oxide of the Group 4b metals zirconium, hafnium, and titanium, or the Group 5b metals niobium, tantalum, and vanadium, preferably zirconium oxide, such oxides being treated with sulfuric acid and calcined. The process may also be applied to substituted equivalents, such as methyl phthalic anhydride and toluene.

8 Claims, No Drawings

PROCESS FOR THE PREPARATION OF ANTHRAQUINONE

PRIOR ART

Anthraquinone and its derivatives are widely used in the dye industry and find other applications in the manufacture of hydrogen peroxide and in the paper pulp industry. Anthraquinone is produced industrially by several processes, principally by oxidizing anthracene or from the reaction of butadiene with naphthalene derived naphthoquinone followed by an oxidation. It can also be produced from the reaction of phthalic anhydride with benzene.

Anthracene is available in small quantities from coal tar and is used to make anthraquinone, but purification of the anthracene feed is difficult and expensive, so that this process is undesirable, even though it has been widely used. Another disadvantage of the process is that the supply of anthracene from coal tar is uncertain and it is expected in the future that its use as a source for anthraquinone will be significantly reduced.

At one time, phthalic anhydride and benzene were reacted commercially in a Friedel-Craft reaction using aluminum chloride in order to produce an intermediate compound, ortho benzoyl benzoic acid, which is then converted by acid treatment to anthraquinone. The process consumed large quantities of aluminum chloride and had other disadvantages. Consequently, it is no longer used industrially and new processes have been sought for preparation of anthraquinone.

An alternative to the use of aluminum chloride is found in U.S. Pat. No. 4,379,092. Hydrogen fluoride and boron trifluoride are used to react phthalic anhydride with benzene in the liquid phase. The process consumes substantial amounts of boron trifluoride and is run at below ambient temperatures, thus requiring refrigeration.

Other processes have been proposed. See Kirk-Othmer, Encyclopedia of Chemical Technology, John Wiley & Sons, 1978, 3rd ed., vol. 2, p. 702–707. Among these are the reaction of 1,4 naphthoquinone with 1,3 butadiene followed by the oxidation of tetrahydroanthraquinone to form anthraquinone. Another method is the oxidation of diphenyl methane derivatives to the intermediate ortho benzoyl benzoic acid, which is subsequently converted to anthraquinone, as shown in U.S. Pat. No. 4,036,860.

The reaction of phthalic anhydride and benzene in a vapor phase reaction in the presence of various catalysts also has been proposed. The catalysts disclosed include silica plus amphoteric metal oxides, including zirconium oxide, as seen in U.S. Pat. No. 2,401,225. Titanium and/or tin oxides have been proposed as catalysts for this reaction in U.S. Pat. No. 4,459,234, which suggests that sulfuric acid treatment may be helpful in improving the activity of these catalysts. A group of Japanese published applications also show metal oxides used as catalysts for this reaction. Japanese Kokai No. 57-70833 discloses the use of boria as the principal metal oxide, in combination with titanium, zirconium, tin, aluminum, tungsten, or lead oxides. A titania-boria catalyst is shown in Example 1 to convert phthalic anhydride in a nitrogen carrier gas to anthraquinone. Japanese Kokai No. 57-70832 is directed specifically to the use of the combination of silica, alumina and boria. In Example 1 phthalic anhydride in a nitrogen carrier gas is passed over such a catalyst. Still another Japanese Kokai No. 57-31637 discloses the use of magnesium and silicon as oxides or sulfates, with many other metal oxides suggested as additives, including zirconium oxide.

Hino, et al. (in J. Chem. Soc., Chem. Commun., 1985, p. 112) disclosed a super acid catalyst prepared by contacting $Zr(OH)_4$ with sulfuric acid followed by calcination as useful in the acylation of toluene with benzoic anhydride to produce methyl benzophenone. Such super acid catalysts are considered to be among the most acidic solid materials presently available.

Despite the many disclosures of processes by which anthraquinone may be prepared and the commercial interest in such processes, those skilled in the art continue to search for improved methods of preparation. The present invention discloses an improved process by which anthraquinone may be prepared from phthalic anhydride and benzene by a liquid phase reaction over a catalyst.

SUMMARY OF THE INVENTION

Anthraquinone is produced by reacting phthalic anhydride with benzene in the liquid phase over a catalyst. The catalyst will consist of at least one oxide from the group consisting of the Group 4b metals zirconium, hafnium, and titanium, and the Group 5b metals niobium, tantalum, and vanadium. Such oxides are treated with a source of a sulfate moiety, such as sulfuric acid, and then calcined; such catalysts are termed "super acid" catalysts. The reaction is carried out at a temperature of about 160° to 280° C., preferably 180° to 200° C. and at a pressure of about 8 to 50 bar, preferably 10–15 bar, said temperature and pressure being selected to maintain the phthalic anhydride in the liquid phase. The process is also applicable to the analogous reactions between substituted equivalents of phthalic anhydride and benzenes, such as methyl phthalic anhydride and toluene.

DESCRIPTION OF THE PREFERRED EMBODIMENTS

Catalysts

The prior art suggests that phthalic anhydride will react with benzene to form anthraquinone in the vapor phase. However, as shown in co-pending U.S. patent application, Ser. No. 883,232, benzene does not react with phthalic anhydride in the vapor phase but instead two molecules of phthalic anhydride react to form anthraquinone and carbon dioxide.

It has now been found that the "super acid" catalysts are capable of reacting phthalic anhydride and benzene, or substituted benzenes, in the liquid phase. The reaction of two molecules of phthalic anhydride found to predominate in the vapor phase does not occur to a significant extent in the liquid phase. It has also been found that the untreated metal oxide catalysts which can be used for the vapor phase reaction have substantially no activity in the liquid phase reaction.

The catalysts may be called "super acid" catalysts. As used here, the term "super acid" catalyst refers to materials having a Hammett acidity of less than $-12.0$, R. Gillespie and T. Peel, J. Am. Chem. Soc. 95, 5173 (1973). The catalysts used in the invention are one or more members of a group of metal oxides which have been treated with a source of sulfate moieties, particularly sulfuric acid, and then calcined to produce a catalyst having an acid strength of less than $-16.04$, as measured photometrically by color change of weak bases (e.g. 2,4-dinitrofluorobenzene) when coordinated to acid sites on the catalyst.

Various metal oxides have been found to be useful, including the Group 4b metals zirconium, hafnium, and titanium, and the Group 5b metals niobium, vanadium, and tantalum. Zirconium oxide is particularly useful. These metal oxides may be used alone or in combination. They are converted to super acid catalysts by reaction with a source of sulfate moieties, particularly sulfuric acid, followed by calcination in air at temperatures in the range of 500° to 700° C., preferably 600° to 620° C.

The following example will provide a typical preparation of a zirconium super acid catalyst useful in the preparation of anthraquinone.

EXAMPLE 1

Catalyst Preparation

Zirconyl chloride octahydrate (504 gm) is dissolved in 1.65 liters of deionized water and mixed with 0.4 liters of 28 wt. % ammonium hydroxide solution over a period of 30 minutes. Insoluble $Zr(OH)_4$ precipitates, after which the solids are recovered by filtration and then reslurried four times with 1.2 liter increments of deionized water. The washed solids are dried at 80° C. for 15 hours. Then, they are stirred with 0.5 liters of 1N sulfuric acid for three hours and recovered by filtration. The solids are calcined at 620° C. in air for three hours, after which time the catalyst is ready for use. Typically the catalyst will contain 1.2–1.4 wt. % sulfur and have a surface area of 100–140 $m^2/gm$.

Although in the foregoing example the catalyst was prepared from zirconyl chloride, it is also feasible to use zirconium oxides, $ZrO_2$, from other water soluble sources, such as zirconyl nitrate hydrate, zirconium(IV) nitrate, and zirconium(IV) chloride.

Sulfuric acid is the preferred acid but other sulfate sources could be used, such as chlorosulfuric acid, fluorosulfuric acid, sulfur trioxide, sulfur dioxide plus oxygen, or solid ammonium sulfate. The concentration of the acid may vary from 0.1 to about 5 molar; at higher concentrations zirconium(IV) is dissolved. The amount of acid needed preferably is greater than that needed to provide sulfates species, the amount used being generally about 0–2 wt. percent sulfur. Contacting of the zirconium oxide and the acid typically will require about 1 to 200 minutes, but is not believed to be critical.

It has been found that the calcination temperature is an important factor in establishing the activity of the resulting catalyst for producing anthraquinone from phthalic anhydride. Although temperatures in the range of 400° to 750° C. may be used, the maximum temperature preferably will be in the range of 550° to 650° C., especially 600° to 620° C. The optimum temperature may vary, depending upon the metal oxide and the acid used.

The catalyst may be used in the powdered form produced in Example 1, or it may be pelletized, extruded, or otherwise compacted for use in commercial applications.

Promoters are not required, but may include such elements as the oxides of molybdenum, tungsten, chromium, or manganese.

Process

It is unique to the process of the invention that phthalic anhydride reacts with benzene in the liquid phase to produce anthraquinone. The molar ratio of benzene to phthalic anhydride should be at least 1:1, but higher ratios may be used, up to 1:100 or even higher.

The reaction may be carried out in a batchwise or continuous manner. The temperature and pressure will be established to maintain the phthalic anhydride in the liquid phase as well as to provide conditions under which the reaction proceeds quickly and efficiently. The temperature may be between about 160° and 280° C., preferably 180°–200° C., while the pressure may be between about 8 and 50 bar, preferably 10–15 bar. If carried out in a batch reactor the catalyst and reactants and any solvents will be maintained at the selected temperature and pressure for a period of up to 3 hours. Conveniently, the reaction is carried out continuously, so that the catalyst is placed in a vessel and contacted with a flowing stream of phthalic anhydride and benzene. A contact time of about 0.1 to 10 minutes may be used. The exiting liquids may be cooled and the anthraquinone product separated by hydrolyzing the unreacted phthalic anhydride and separating the insoluble anthraquinone.

The catalyst may deactivate with use and it has been found that it may be easily regenerated by calcining the catalyst again in air at 500° C.

The following example illustrates one method of carrying out the process of the invention.

EXAMPLE 2

The catalyst of Example 1 was used to prepare methyl anthraquinone by the liquid phase reaction of phthalic anhydride with toluene. Five grams of the catalyst, 4.72 g of phthalic anhydride and 80 ml toluene (dried over 4A molecular sieves) are charged to a 300 cc autoclave, which is then flushed and pressurized to 35.5 bar with nitrogen. The reaction was carried out at 200° C. for 2 hours with stirring. After depressuring and cooling the liquid contents are filtered to recover the solids, which contain the catalyst. The liquid phase is analyzed by gas chromatography to determine the amount of methyl anthraquinone. Ten percent of the phthalic anhydride has been converted with a 57% selectivity to methyl anthraquinone and 43% to by-product orth-di(methyl benzoyl)benzene.

EXAMPLE 3

A titanium super-acid catalyst is prepared by adding titanium chloride (250 g) to 1.25 liters of deionized water and precipitating titanium hydroxide by adding 0.745 liters of 28 wt. % ammonium hydroxide solution. The precipitated titanium hydroxide is filtered and washed with four 0.5 liter increments of water. The recovered $Ti(OH)_4$ is mixed with 0.4 liters of 1N $H_2SO_4$ for three hours, after which the solids are filtered, dried at 80° C. for 15 hours, and calcined in air at 575° C. The catalyst powder is pressed to form wafers and broken to form 4–12 mesh particles. The experiment of Example 2 is repeated using this catalyst Analysis of the products of reaction indicates a 10.8% conversion of phthalic anhydride with a 47% selectivity to methyl anthraquinone and 53% to orth-di(methyl benzoyl)benzene.

EXAMPLE 4

A glass-lined 200 cc Parr bomb is charged with 1.2 g. of phthalic anhydride, 1.0 g of the super-acid catalyst of Example 1, and 20 ml of benzene. After flushing the bomb with nitrogen, it is pressured to 28.6 bar with carbon dioxide. The reaction was then carried out at 200° C. for 2 hours with mixing, following which the bomb is cooled and depressured. The solids are filtered and analyzed and found to contain anthraquinone equivalent to a 5.2% conversion of phthalic anhydride with a 49% selectivity to anthraquinone and 51% selectivity to ortho-dibenzoylbenzene.

EXAMPLE 5

Comparative

The experiment of Example 2 is repeated except that no toluene is included and 20 cc of carbon disulfide is used as a solvent, that is, phthalic anhydride is present. No methyl anthraquinone is found to have been formed.

EXAMPLE 6

Comparative

The experiment of Example 2 is repeated except that instead of the super-acid catalyst, untreated $ZrO_2$ was used as a catalyst. The $ZrO_2$ had been calcined in air at 600° C. for 3 hours and had a surface area of 58 $m^2$/gm. No methyl anthraquinone is found.

What is claimed is:

1. A process for the production of anthraquinone or lower alkyl equivalents comprising:
   (a) reacting phthalic anhydride and benzene or their lower alkyl equivalents to form anthraquinone or lower alkyl anthraquinones and water in the presence of a eatalyst consisting of oxides of at least one member of the group of Group 4b metals zirconium, hafnium, and titanium and the Group 5b metals niobium, tantalum, and vanadium, said catalyst being pretreated with a source of sulfate moieties and calcined at a temperature in the range of 400°-750° C., said reaction being carried out at a temperature in the range of 160°-280° C. and a pressure in the range of 8-50 bar, said temperature and pressure being selected to maintain the phthalic anhydride in the liquid phase;
   (b) separating the anthraquinone produced in step (a).

2. The process of claim 1 wherein said catalyst is sulfuric acid treated and has a Hammett acid strength of less than −16.04.

3. The process of claim 2 wherein the catalyst comprises sulfuric acid treated zirconium oxide.

4. The process of claim 2 wherein the catalyst comprises sulfuric acid treated titanium oxide.

5. The process of claim 1 wherein phthalic anhydride is reacted with benzene.

6. The process of claim 1 wherein phthalic anhydride is reacted with a lower alkyl benzene.

7. The process of claim 1 wherein the reaction temperature is in the range of 180°-200° C.

8. The process of claim 1 wherein the reaction pressure is in the range of 10-15 bar.

* * * * *